United States Patent
Foster et al.

(10) Patent No.: US 9,907,948 B2
(45) Date of Patent: Mar. 6, 2018

(54) ELECTRICAL AND MECHANICAL CONNECTION FOR COILED STIMULATION/SENSING LEAD CONDUCTORS

(71) Applicant: Cardiac Pacemakers, Inc., St. Paul, MN (US)

(72) Inventors: Arthur J. Foster, Blaine, MN (US); Paul E. Zarembo, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 944 days.

(21) Appl. No.: 14/297,978

(22) Filed: Jun. 6, 2014

(65) Prior Publication Data
US 2014/0364713 A1 Dec. 11, 2014

Related U.S. Application Data

(60) Provisional application No. 61/832,559, filed on Jun. 7, 2013.

(51) Int. Cl.
*A61B 5/042* (2006.01)
*A61N 1/05* (2006.01)
*H01R 4/30* (2006.01)

(52) U.S. Cl.
CPC ............... *A61N 1/05* (2013.01); *A61B 5/042* (2013.01); *A61B 2562/227* (2013.01); *H01R 4/30* (2013.01); *Y10T 29/4902* (2015.01); *Y10T 29/49174* (2015.01)

(58) Field of Classification Search
CPC ........ A61N 1/05; A61N 1/0551; A61N 1/056; A61N 1/0563; A61N 1/3752; A61N 1/3754; A61B 5/042; A61B 5/0408; A61B 5/0492; A61B 5/686; A61B 2562/125; A61B 2562/22; A61B 2562/225; A61B 2562/227; H01R 4/30
USPC .............................................. 29/825; 439/801
See application file for complete search history.

(56) References Cited

U.S. PATENT DOCUMENTS

| | | | | |
|---|---|---|---|---|
| 4,328,812 A | * | 5/1982 | Ufford | A61N 1/056 607/122 |
| 4,538,623 A | | 9/1985 | Proctor et al. | |
| 4,614,395 A | | 9/1986 | Peers-Trevarton | |
| 4,730,389 A | * | 3/1988 | Baudino | A61B 5/14552 204/424 |
| 4,938,822 A | | 7/1990 | Peers-Trevarton | |

(Continued)

FOREIGN PATENT DOCUMENTS

EP 1023915 B1 8/2000

*Primary Examiner* — Lee S Cohen
*Assistant Examiner* — Erin M Cardinal
(74) *Attorney, Agent, or Firm* — Faegre Baker Daniels LLP

(57) ABSTRACT

A medical electrical lead includes a threaded conductor, a coil conductor, and a sleeve. The threaded conductor has an outer surface with a threaded section that includes threads defining grooves between the threads. The coil conductor has coils seated in the grooves of the threaded conductor. The coil conductor has a coil major diameter greater than a thread major diameter. The sleeve is positioned radially outward of the coil conductor and has an inner surface in contact with the coil conductor so as to produce a radially inward force compressing the coil conductor against the threaded section of the threaded conductor.

18 Claims, 14 Drawing Sheets

(56) References Cited

U.S. PATENT DOCUMENTS

| | | | |
|---|---|---|---|
| 5,014,720 A | 5/1991 | Barcel et al. | |
| 5,231,996 A | 8/1993 | Bardy et al. | |
| 5,423,876 A | 6/1995 | Camps et al. | |
| 5,490,323 A * | 2/1996 | Thacker | A61N 1/056 29/825 |
| 5,522,874 A | 6/1996 | Gates | |
| 5,522,875 A | 6/1996 | Gates et al. | |
| 5,571,157 A | 11/1996 | McConnell | |
| 5,852,872 A | 12/1998 | Walter et al. | |
| 5,954,759 A * | 9/1999 | Swoyer | A61N 1/056 607/122 |
| 6,026,567 A * | 2/2000 | Swoyer | A61N 1/05 29/825 |
| 6,148,237 A | 11/2000 | Das | |
| 6,373,024 B1 * | 4/2002 | Safarevich | A61N 1/05 219/121.64 |
| 6,505,081 B1 | 1/2003 | Das | |
| 7,546,165 B2 | 6/2009 | Zarembo et al. | |
| 7,831,311 B2 | 11/2010 | Cross, Jr. et al. | |
| 2008/0057784 A1 * | 3/2008 | Zarembo | A61N 1/056 439/592 |
| 2008/0154293 A1 * | 6/2008 | Taylor | A61B 17/32053 606/170 |
| 2008/0200078 A1 * | 8/2008 | Waltz | H01R 4/20 439/783 |
| 2009/0149053 A1 * | 6/2009 | Chansrivong | H01R 13/15 439/349 |
| 2009/0186521 A1 * | 7/2009 | McMullen | H01R 9/0521 439/578 |
| 2009/0222074 A1 * | 9/2009 | Zarembo | A61N 1/056 607/126 |
| 2010/0015848 A1 * | 1/2010 | Huang | H01R 13/72 439/501 |
| 2010/0137928 A1 | 5/2010 | Duncan | |
| 2010/0279558 A1 * | 11/2010 | Leon | H01R 13/17 439/817 |
| 2011/0071610 A1 | 3/2011 | Haiping Shat et al. | |
| 2011/0124245 A1 * | 5/2011 | Fujita | H01R 13/17 439/840 |
| 2012/0028512 A1 * | 2/2012 | Weitzig | A61N 1/056 439/816 |
| 2012/0040547 A1 | 2/2012 | Forslund et al. | |
| 2012/0158108 A1 | 6/2012 | Foster et al. | |

* cited by examiner

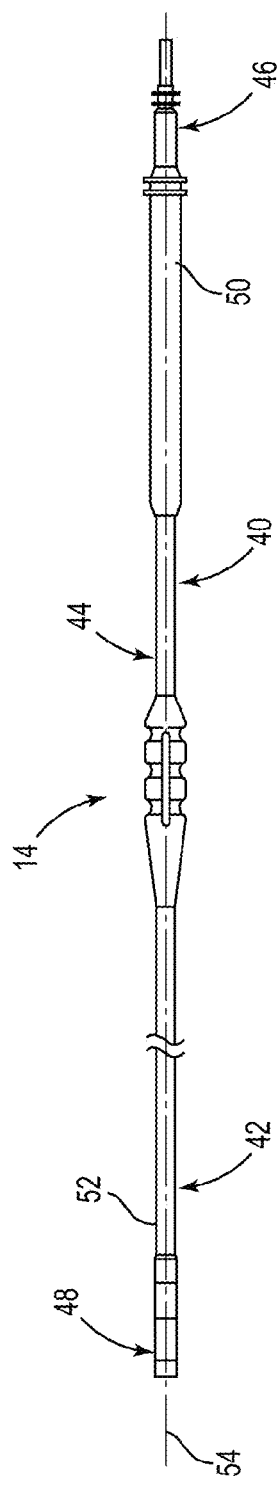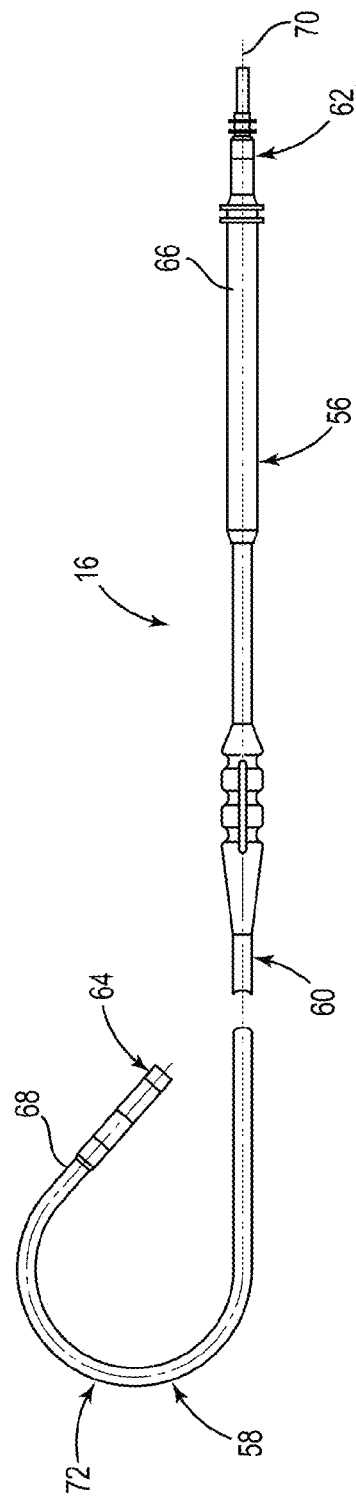

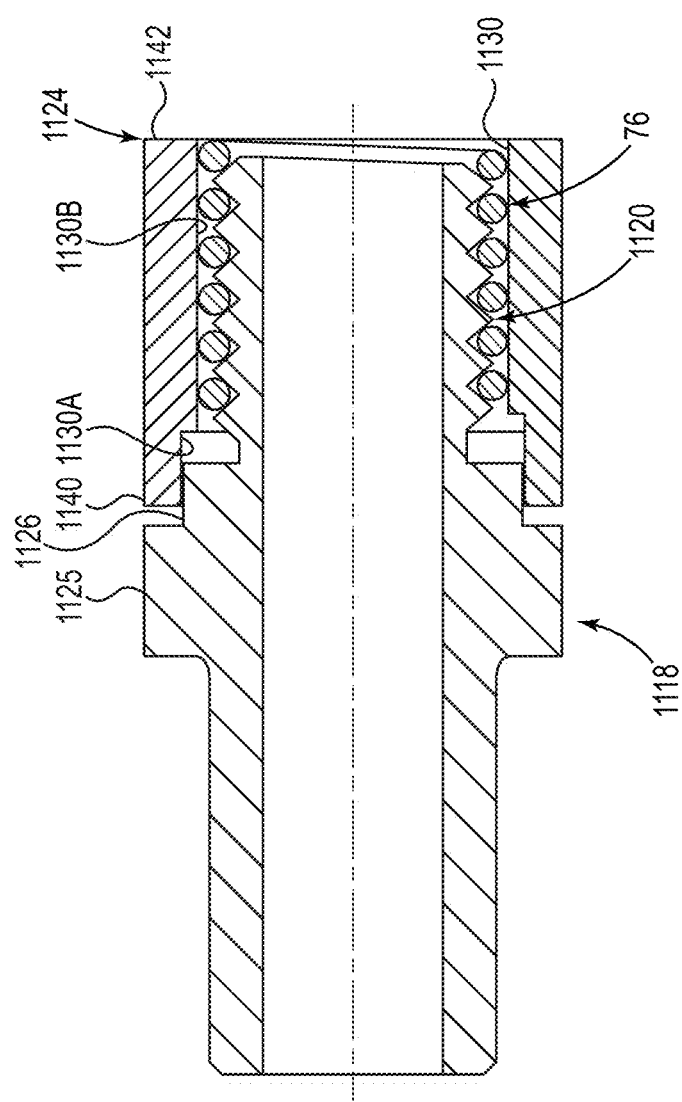

ELECTRICAL AND MECHANICAL CONNECTION FOR COILED STIMULATION/SENSING LEAD CONDUCTORS

CROSS-REFERENCE TO RELATED APPLICATION

This application claims priority to Provisional Application No. 61/832,559, filed Jun. 7, 2013, which is herein incorporated by reference in its entirety.

TECHNICAL FIELD

The present invention relates to implantable medical devices for stimulating body tissues and/or sensing physiological attributes. More specifically, the invention relates to connections within medical electrical leads.

BACKGROUND

Various physiological functions can be managed and/or monitored using medical devices. Many such medical devices include medical electrical leads that can transmit electrical signals to and/or from a sensor, electrode, or other electrical component at a distal end of the medical electrical lead. For example, medical electrical leads have been used in association with neurostimulation and cardiac rhythm management, which can include cardiac pacing, cardiac defibrillation, and/or cardiac therapy, among other procedures. Various designs for such medical electrical leads are known in the art. There exists a need for alternative designs for medical electrical leads that can be used in such medical devices.

SUMMARY

Disclosed herein are various embodiments of medical electrical leads and methods of assembling a medical electrical lead.

In Example 1, a medical electrical lead includes a threaded conductor, a coil conductor, and a sleeve. The threaded conductor has an outer surface with a threaded section that includes threads that are helical and that define grooves between the threads. The coil conductor has coils seated in the grooves of the threaded conductor. The coil conductor has a coil major diameter greater than a thread major diameter. The sleeve is positioned radially outward of the coil conductor and has an inner surface in contact with the coil conductor so as to produce a radially inward force compressing the coil conductor against the threaded section of the threaded conductor.

In Example 2, the medical electrical lead according to Example 1, wherein the coil conductor is welded to the threaded section.

In Example 3, the medical electrical lead according to any of Examples 1 or 2, wherein the sleeve comprises a plurality of ridges extending radially inward from the inner surface in contact with the coil conductor.

In Example 4, the medical electrical lead according to any of Examples 1-3, wherein the threaded conductor has a ridged section adjacent the threaded section.

In Example 5, the medical electrical lead according to Example 4, wherein the ridged section has a plurality of ridges extending radially outward from the outer surface in an axial direction with respect to a centerline axis of the threaded conductor, and wherein the coil conductor is compressed between the ridges and the sleeve.

In Example 6, the medical electrical lead according to any of Examples 4 or 5, wherein the ridged section has a knurled pattern.

In Example 7, the medical electrical lead according to any of Examples 1-6, wherein at least one of the threaded section and the inner surface is substantially conical.

In Example 8, the medical electrical lead according to any of Examples 1-7, wherein both the threaded section and the inner surface are substantially conical.

In Example 9, the medical electrical lead according to any of Examples 1-8, wherein the inner surface of the sleeve is spaced from the threads.

In Example 10, the medical electrical lead according to any of Examples 1-9, wherein at least one of the threaded conductor and the sleeve comprises an electrode for delivering an electrical stimulation to or for sensing an electrical signal from body tissue.

In Example 11, the medical electrical lead according to any of Examples 1-10, wherein the threaded conductor and the sleeve combine to form a ring electrode assembly.

In Example 12, the medical electrical lead according to any of Examples 1-11, wherein the threaded conductor comprises at least one bump extending radially outward from the outer surface between threads in contact with the coil conductor.

In Example 13, the medical electrical lead according to any of Examples 1-12, and further including a seal ring positioned axially between the sleeve and an outer ring of the threaded conductor, wherein the seal ring is hermetically welded between the sleeve and the threaded conductor.

In Example 14, a method of assembling a medical electrical lead includes threading a coil conductor between threads on a threaded surface of a threaded conductor. Coils of the coil conductor are positioned at least partially in grooves between the threads with a portion of the coils extending radially outward from the radially outer extent of the threads. A sleeve is pressed axially over the coil conductor so as to form an interference fit with the coils positioned partially in the grooves.

In Example 15, the method of Example 14, and further including welding the coil conductor to the threads of the threaded conductor prior to sliding the sleeve over the coil conductor.

In Example 16, the method according to any of Examples 14 or 15, wherein the coil conductor has a layer of insulation, wherein the threaded conductor comprises at least one ridge extending radially outward from the threaded conductor, and wherein pressing the sleeve axially over the coil conductor causes the ridge to cut through the layer of insulation to contact the coil conductor.

In Example 17, a medical electrical lead includes a first conductor, a coil conductor, and a second conductor. The first conductor has a threaded section that includes threads that are helical and that define grooves between the threads. At least one of the threads comprises a bump that distorts a helical path between the threads. The coil conductor has coils seated in the grooves between the threads of the first conductor. The bump bends one of the coils of the coil conductor. The second conductor is axially aligned with the threaded section of the first conductor. The coils of the coil conductor are positioned between the first conductor and the second conductor.

In Example 18, the medical electrical lead of Example 17, wherein the bump is one of a plurality of bumps extending axially from the threads. The threads further include a plurality of recesses each aligned opposite of one of the plurality of bumps.

In Example 19, the medical electrical lead of any of Examples 17 or 18, wherein an interference fit compresses the coil conductor between the second conductor and the threaded section.

In Example 20, the medical electrical lead of any of Examples 17-19, wherein the threads extend from an outer surface of the first conductor and wherein the second conductor is a sleeve positioned radially outward of the first conductor.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 2A is a side view of a lead of the CRM system of FIG. 1.

FIG. 2B is a side view of another lead of the CRM system of FIG. 1.

FIG. 14 is a schematic cross-sectional view of another alternative embodiment of a threaded conductor and a corresponding sleeve.

Figure 1:
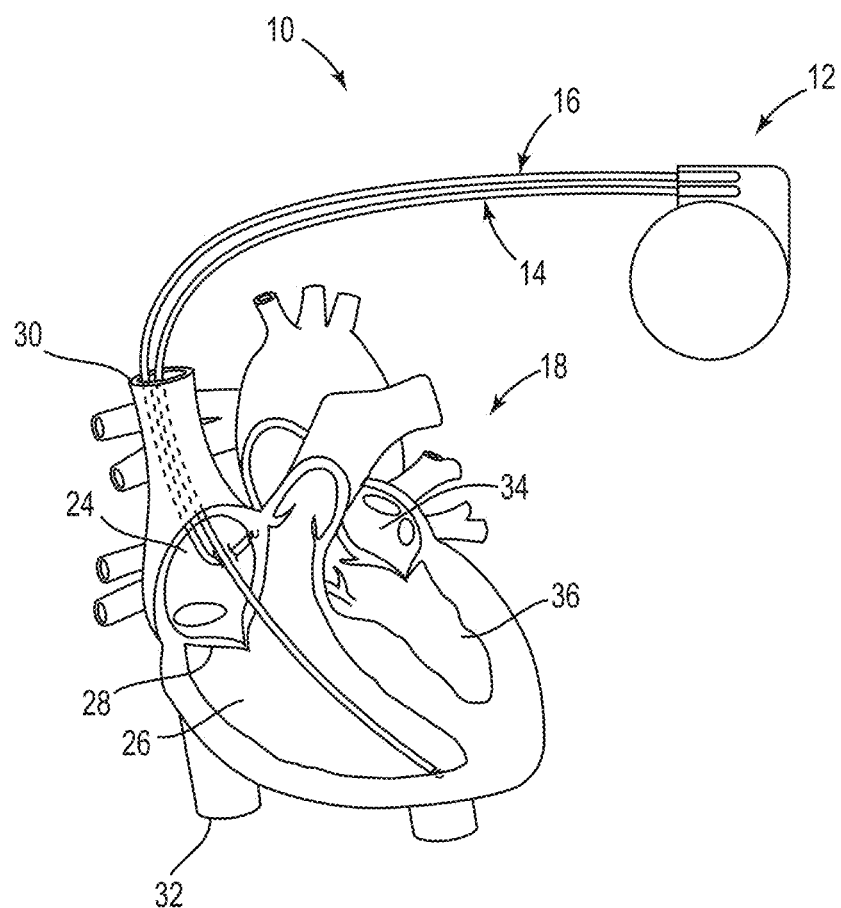
FIG. 1 is a schematic view of a cardiac rhythm management (CRM) system according to one embodiment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a cardiac rhythm management (CRM) system 10 according to one embodiment. As shown in FIG. 1, the CRM system 10 includes a pulse generator 12 coupled to a plurality of leads 14, 16 deployed in a patient's heart 18. As further shown in FIG. 1, the heart 18 includes a right atrium 24 and a right ventricle 26 separated by a tricuspid valve 28. During normal operation of the heart 18, deoxygenated blood is fed into the right atrium 24 through the superior vena cava 30 and the inferior vena cava 32. As further shown, the heart 18 includes a left atrium 34, which receives oxygenated blood from the lungs, and a left ventricle 36, which pumps the oxygenated blood to the body.

The leads 14, 16 are medical electrical leads that operate to convey electrical signals and stimuli between the heart 18 and the pulse generator 12. In the illustrated embodiment, the lead 14 is implanted in the right ventricle 26, and the lead 16 is implanted in the right atrium 24. In other embodiments, the CRM system 10 may include additional leads, e.g., a lead extending into a coronary vein for stimulating the left ventricle in a bi-ventricular pacing or cardiac resynchronization therapy (CRT) system and/or a lead for defibrillation (e.g., an S-ICD lead). As shown, the leads 14, 16 enter the superior vena cava 30, and are implanted in the right ventricle 26 and right atrium 24, respectively. Embodiments of the present disclosure can also be used in neurostimulation systems including spinal stimulation, nerve stimulation, etc.

The pulse generator 12 can be implanted subcutaneously within an implantation location or pocket in the patient's chest or abdomen. The pulse generator 12 can be an implantable medical device known in the art, or later developed, for delivering an electrical therapeutic stimulus to the patient. In various embodiments, the pulse generator 12 can be a pacemaker, a CRT device, a subcutaneous implantable cardiac defibrillator (e.g., a S-ICD device), and/or includes both pacing, CRT and/or defibrillation capabilities (e.g., a CRT-D device). In other embodiments the pulse generator 12 can be a neurostimulation device.

In some embodiments the electrodes of the CRM system 10 can be configured to stimulate cardiac tissue and/or sense certain physiological attributes of the heart. However, in discussing embodiments of the present disclosure, reference is made primarily to electrodes stimulating body tissues. Those of ordinary skill in the art will recognize that some or all of the electrode configurations can also be used to receive electrical signals from the body.

FIG. 2A is a side view of the lead 14 in a non-implanted state. As shown in FIG. 2A, the lead 14 is defined by a proximal region 40 and a distal region 42. Generally speaking, the proximal region 40 is dimensioned so as to make up the portion of the lead 14 extending from the pulse generator 12 to the location at which the lead 14 enters the right atrium 24 via the superior vena cava 30, whereas the distal region 42 is dimensioned to extend within the heart 18 to the location at which the lead 14 is attached to the endocardium (see FIG. 1).

In the embodiment illustrated in FIG. 2A, the lead 14 includes a flexible body 44, a proximal connector 46, and a distal tip assembly 48. As shown, the body 44 includes a proximal end 50 and an opposite distal end 52. The proximal connector 46 is coupled to the proximal end 50 of the body 44, and the distal tip assembly 48 is coupled to the distal end 52 of the body 44. In the illustrated embodiment, the elongate body 44 defines a longitudinal axis 54 of the lead 14.

FIG. 2B is a side view of the lead 16 in a non-implanted state. As shown in FIG. 2B, the lead 16 is in many respects similar or identical to the lead 14, and has a proximal region 56 and a distal region 58. Additionally, the lead 16 includes a flexible, elongate body 60, a proximal connector 62, and a distal tip assembly 64. As shown, the body 60 has a proximal end 66 and a distal end 68 opposite the proximal end 66. The proximal connector 62 is coupled to the proximal end 66 of the body 60, and the distal tip assembly 64 is coupled to the distal end 68 of the body 60, as in the lead 14. Similar to the lead 14, the lead body 60 defines a longitudinal axis 70 of the lead 16. As can be seen in FIG. 2B, the lead 16 primarily differs structurally from the lead 14 in that the distal region 58 of the lead 16 includes a pre-formed curved portion 72 shaped into a J-shape to direct the tip assembly 64 toward a desired attachment location within the right atrium 24. The leads 14, 16 are otherwise generally identical, and so for expediency, various embodiments of the lead 14 will be described herein, although it is emphasized that the described features and functionality can be readily applied to a right atrial lead such as the lead 16.

Figure 3A:
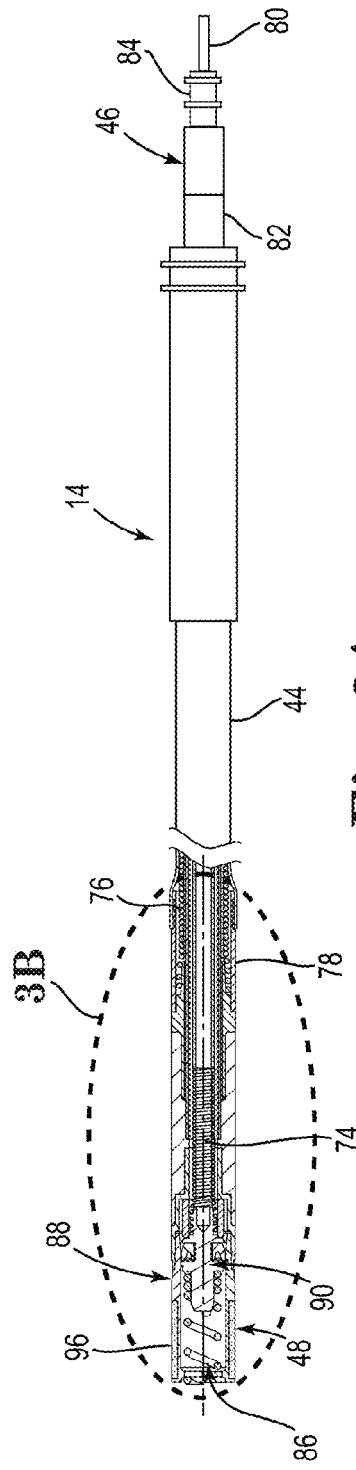
FIGS. 3A and 3B are partial cross-sectional views of the lead of FIG. 2A according to an exemplary embodiment.
Figure 3B:
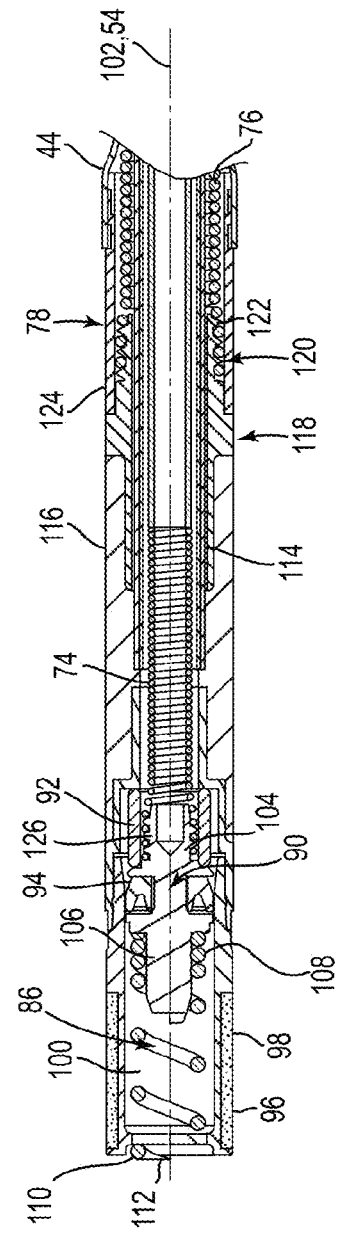

FIGS. 3A and 3B are partial cross-sectional views of the lead 14 according to an exemplary embodiment. As shown in FIGS. 3A and 3B, the lead 14 includes, in the illustrated exemplary embodiment, an inner coil conductor 74, an outer coil conductor 76, and a ring electrode assembly 78. Additionally, the connector 46 includes a terminal pin 80, a ring contact 82, and a seal member 84. In the illustrated embodiment, the connector 46 is a conventional bi-polar connector, e.g., an IS-1 connector, configured to mechanically and electrically couple the lead 14 to a header of the pulse generator 12 (see FIG. 1). As such, the ring contact 82 and the terminal pin 80 are each electrically conductive and electrically isolated from one another, and are adapted to engage a corresponding contact within the pulse generator header. In one embodiment, the terminal pin 80 is rotatable relative to the ring contact 82 and the lead body 44, and is operable to facilitate extension and retraction of a fixation helix/electrode 86 housed within the distal tip assembly 48. However, other embodiments may utilize other configurations for the connector 46, depending on the configuration of the corresponding pulse generator 12. Additionally, other embodiments may omit the fixation helix 86, and instead use alternative electrodes and means for fixing.

As further shown, in the illustrated embodiment, the distal tip assembly 48 includes a shell 88, a coupler 90, a sleeve 92, a seal member 94, a drug collar 96, and the fixation helix 86. As illustrated, the shell 88 includes an outer wall 98 enclosing an internal cavity 100, and has a longitudinal axis 102 generally corresponding to the longitudinal axis 54 of the lead 14.

In the illustrated embodiment, the coupler 90 operates as a rotatable shaft, and thus is rotatably disposed within the cavity 100 and includes a proximal shaft portion 104 and a distal shaft portion 106.

In the embodiment of FIGS. 3A and 3B, the fixation helix 86 has a proximal portion 108 and a distal portion 110 terminating in a sharpened distal tip 112. As shown, the proximal portion 108 of the fixation helix 86 is coupled to the distal shaft portion 106 of the coupler 90. In the illustrated embodiment, both the coupler 90 and the fixation helix 86 are made of an electrically conductive material.

The lead body 44 is in the form of a flexible, elongate tube of electrically insulative material, and the inner and outer coil conductors 74, 76 extend longitudinally within the lead body 44. In the illustrated embodiment, the coil conductors 74, 76 are configured in a coaxial, non-coradial configuration as is known in the art. Additionally, a tubular inner insulating sheath 114 is disposed between the inner and outer conductor coils 74, 76. However, in various embodiments, e.g., those in which the inner and outer coil conductors 74, 76 are separately insulated, the inner insulating sheath 114 may be omitted. In the illustrated embodiment, the lead body 44 is a multi-part structure and includes a distal segment 116 between the ring electrode assembly 78 and the distal tip assembly 48. However, in other embodiments, the lead body 44 may be a single, unitary tubular element.

In addition, although not visible in FIG. 3A or 3B, the inner and outer coil conductors 74, 76 are both mechanically and electrically connected to the terminal pin 80 and the ring contact 82, respectively, within the connector 46. Because the terminal pin 80 is rotatable relative to the lead body 44, the inner conductor 74 is also rotatable within the lead body 44 and can operate as a torque transmission member to transmit torque applied at the terminal pin 80 to the coupler 90 and the fixation helix 86.

As illustrated, the outer coil conductor 76 is both mechanically and electrically connected to the ring electrode assembly 78, which operates as a low-voltage pace/sense electrode. The ring electrode assembly 78 includes a threaded conductor 118 having a threaded section 120 with threads 122 extending radially outward from and helically around the threaded section 120. The outer coil conductor 76 is engaged with the threaded section 120 such that coils of the outer coil conductor 76 are positioned between the threads 122. The ring electrode assembly 78 also includes a sleeve 124 positioned radially outward of the outer coil conductor 76 and the threaded section 120. The sleeve 124 has a tight, interference fit with the outer coil conductor 76 that produces a radially inward force compressing the outer coil conductor 76 against the threaded section 120 of the threaded conductor 118. The outer coil conductor 76 can also be welded to one or both of the sleeve 124 and the threaded section 120. Thus, because both the threaded conductor 118 and the sleeve 124 are electrically conductive, the outer coil conductor 76 is configured to transmit electrical signals and/or stimuli between the ring contact 82 and the ring electrode assembly 78.

As also illustrated, the inner coil conductor 74 is fixedly coupled, both mechanically and electrically, to the proximal shaft portion 104 of the coupler 90. The proximal shaft portion 104 is a threaded section with threads 126 extending radially outward from and helically around the proximal shaft portion 104. The inner coil conductor 74 is engaged with the proximal shaft portion 104 such that coils of the inner coil conductor 74 are position between the threads 126. The sleeve 92 is positioned radially outward of the inner coil conductor 74 and the proximal shaft portion 104. The sleeve 92 has a tight, interference fit with the inner coil conductor 74 that produces a radially inward force compressing the inner coil conductor 74 against the threads 126 of the proximal shaft portion 104. The inner coil conductor 74 can also be welded to one or both of the sleeve 92 and the proximal shaft portion 104. Thus, because both the coupler 90 and the fixation helix 86 are electrically conductive, the inner coil conductor 74 is configured to transmit electrical signals and/or stimuli between the terminal pin 80 and the fixation helix 86, which operates as a low voltage pace/sense electrode. Consequently, in the illustrated embodiment, the ring electrode assembly 78 and the fixation helix 86 combine to provide bi-polar pacing and sensing capabilities.

Figure 4:
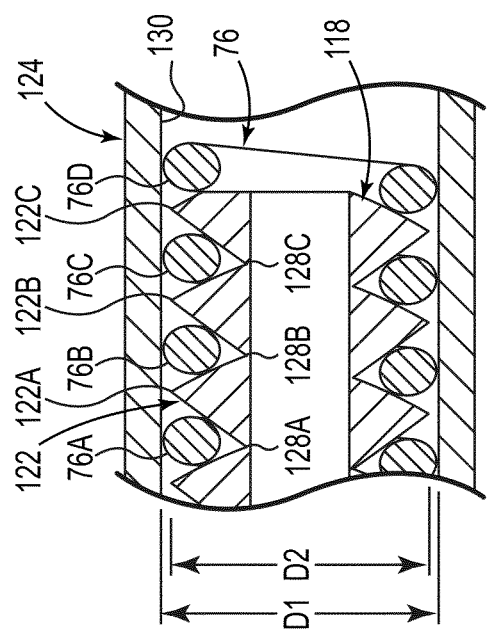
FIG. 4 is a schematic cross-sectional view of a connection between a coil conductor and a threaded conductor in the lead of FIGS. 2A-3B.

FIG. 4 is a schematic partial cross-sectional view of a connection between the outer coil conductor 76, the threaded conductor 118, and the sleeve 124. The threads 122 define grooves 128 between the threads 122. The threads 122 include in series: a thread 122A positioned distal from a thread 122B, which is positioned distal from a thread 122C. A groove 128A is distal of the thread 122A, a groove 128B is between the threads 122A and 122B, and a groove 128C is between the threads 122B and 122C. The outer coil conductor 76 includes a coil 76A positioned in the groove 128A, a coil 76B positioned in the groove 128B, a coil 76C positioned in the groove 128C, and a coil 76D extending in a proximal direction from the threaded conductor 118. In the illustrated embodiment, the threads 122 are V-threads and the grooves 128 are V-grooves. In alternative embodiments, the shape of the threads 122 and grooves 128 can be varied, such as square threads and grooves or U-grooves, among other shapes.

The sleeve 124 has a radially inner surface 130 in contact with the outer coil conductor 76. The sleeve 124 exerts a radially inward force on the outer coil conductor 76, pressing the coils 76A, 76B, and 76C into the grooves 128A, 128B, and 128C, respectively, and against the threaded conductor 118. Each of the coils 76A, 76B, and 76C are thus held in contact against three surfaces. For example, the coil 76B is in contact with the thread 122A, the thread 122B, and the radially inner surface 130 of the sleeve 124.

The coils 76A, 76B, and 76C of the outer coil conductor 76 have a coil major diameter of $D_1$. The threads 122A, 122B, and 122C have a thread major diameter $D_2$. In the illustrated embodiment, the coil major diameter $D_1$ is greater than the thread major diameter $D_2$. Thus, the coils 76A, 76B, and 76C are positioned partially in the grooves 128A, 128B, and 128C and partially extend radially outward past the radially outer extent of the threads 122A, 122B, and 122C. Thus, when the sleeve 124 is assembled with the outer coil conductor 76 and the threaded conductor 118, the sleeve 124 has a diameter substantially equal to the coil major diameter $D_1$ and is spaced from the threads 122 of the threaded conductor 118. The sleeve 124 has an interference fit with the outer coil conductor 76, but need not have an interference fit with the threads 122. In an alternative embodiment, the thread major diameter $D_2$ can be substantially equal to the coil major diameter $D_1$ such that the sleeve 124 has an interference fit with both the outer coil conductor 76 and the threads 122 of the threaded conductor 118.

In one embodiment, assembly can be performed by first attaching the outer coil conductor 76 to the threaded conductor 118. Either or both of the outer coil conductor 76 and the threaded conductor 118 can be rotated so as to screw or thread the coils 76A, 76B, and 76C of the outer coil conductor 76 between the threads 122A, 122B, and 122C of the threaded conductor 118. The coils 76A, 76B, and 76C can then be welded to the threads 122A, 122B, and 122C. The sleeve 124 can then be forced axially to be pressed on the coils 76A, 76B, and 76C so as to have an interference fit. The sleeve 124 is forced axially over the coils 76A, 76B, and 76C but then exerts a radially inward force on the coils 76A, 76B, and 76C once in place. Thus, in this embodiment, the threaded conductor 118 is connected to the outer coil conductor 76 via three mechanisms: threads, welding, and an interference fit. Such a connection can provide a strong and reliable mechanical and electrical connection between the outer coil conductor 76 and the threaded conductor 118.

In the illustrated embodiment, both the threaded conductor 118 and the sleeve 124 are made of electrically conductive material. In an alternative embodiment, the threaded conductor 118 can be made of electrically conductive material and the sleeve 124 can be made of non-conductive material. Alternatively, the sleeve 124 can be made of an electrically conductive material and the threaded conductor 118 can be replaced with a non-conductive component. In either case, the outer coil conductor 76 can be held by an interference fit between radially inner and outer components.

In FIG. 4, the threads 122 are illustrated as extending radially outward from the threaded conductor 118. In alternative embodiments, the threads 122 can instead extend radially inward from the sleeve 124. In such embodiments, the outer coil conductor 76 can be welded to the threads 122 on the sleeve 124 and/or to a non-threaded surface on the threaded conductor 118 (which may or may not be threaded in such embodiments).

Although the connection illustrated in FIG. 4 is described with respect to the outer coil conductor 76, the threaded conductor 118, and the sleeve 124, such a connection can be performed elsewhere in the leads 14, 16 of the CRM system 10. For example, in the illustrated embodiment (shown in FIGS. 3A and 3B) the inner coil conductor 74 is threadedly engaged with the threads 126 of the proximal shaft portion 104 of the coupler 90, and the sleeve 92 is pressed on to provide an interference fit. The inner coil conductor 74 can be welded to the proximal shaft portion 104 as well to provide three mechanisms of connection: threads, welding, and an interference fit.

In some embodiments, one or both of the inner and outer coil conductors 74, 76 can be connected to the terminal pin 80 and the ring contact 82, respectively, via threads, welding, and an interference fit. In other embodiments, the inner and outer coil conductors 74, 76 can be connected to the terminal pin 80 and the ring contact 82, respectively, in another way. For example, the inner and outer coil conductors 74, 76 can be connected to the terminal pin 80 and the ring contact 82, respectively, via threads and an interference fit, without welding.

Figure 5B:
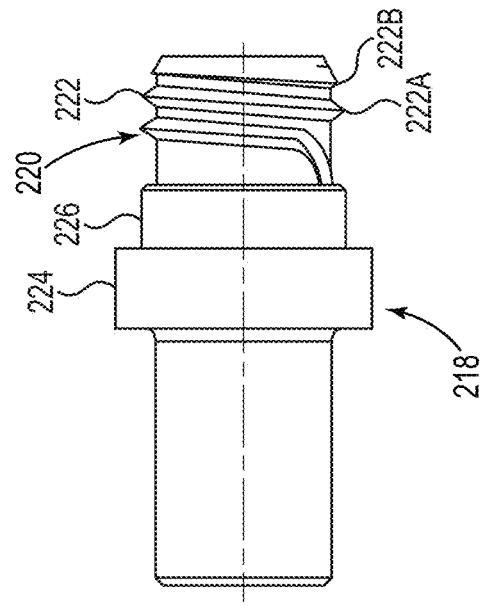
FIG. 5B is a side view of the threaded conductor of FIG. 5A.
Figure 5A:
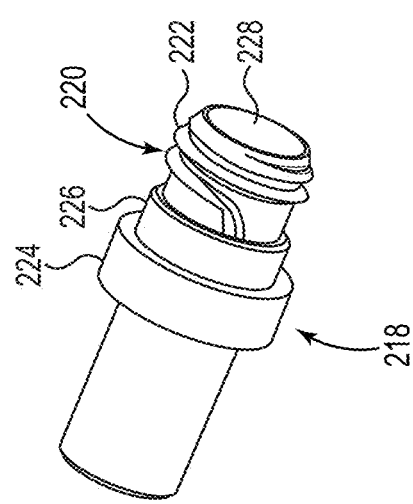
FIG. 5A is an isometric view of an alternative embodiment of a threaded conductor.

FIG. 5A is an isometric view of a threaded conductor 218, which is an alternative embodiment of the threaded conductor 118 (shown in FIGS. 3A, 3B, and 4). The threaded conductor 218 has a threaded section 220 with threads 222 extending radially outward from and helically around the threaded section 220. An outer ring 224 is a substantially cylindrical ring that defines the radially outer extent of the threaded conductor 218. A shoulder 226 is positioned axially between the outer ring 224 and the threaded section 220. The shoulder 226 is substantially cylindrical, with a diameter less than that of the outer ring 224 but greater than that of the threaded section 220. The threaded conductor 218 has an inner surface 228 defining a lumen extending through the threaded conductor 218.

FIG. 5B is a side view of the threaded conductor 218, showing the threads 222 as including threads 222A and 222B. The threaded section 220 tapers in the proximal direction, such that the thread 222A has a larger diameter than that of the thread 222B. Because the threaded section 220 is tapered, it has a substantially frustoconical shape. Thus, when a coil conductor (such as the outer coil conductor 76) and a sleeve (such as the sleeve 124) are attached to the threaded conductor 218, the interference fit by the sleeve 124 can be tighter against certain individual coils (such as the coil 76A) than against other individual coils (such as the coil 76B) positioned in the proximal direction.

Figure 6B:
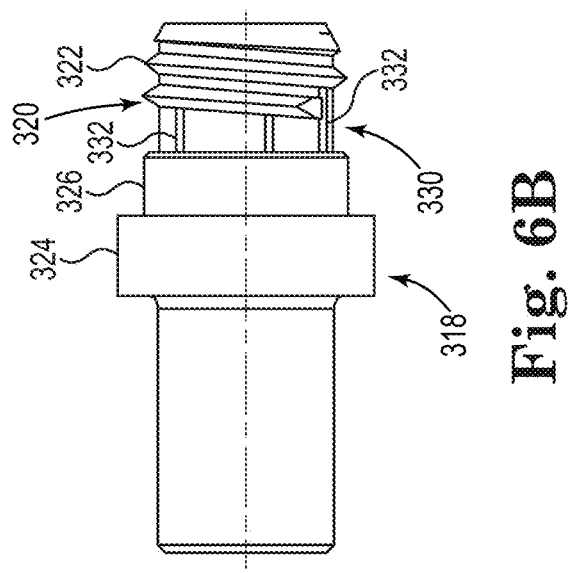
FIG. 6B is a side view of the threaded conductor of FIG. 6A.
Figure 6A:
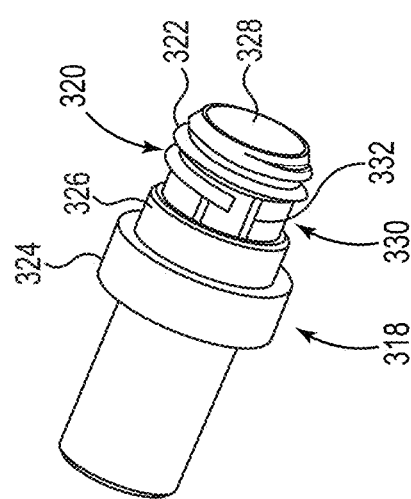
FIG. 6A is an isometric view of another alternative embodiment of a threaded conductor.

FIG. 6A is an isometric view of a threaded conductor 318, which is an alternative embodiment of the threaded conductors 118 (shown in FIGS. 3A, 3B, and 4) and 218 (shown in FIGS. 5A and 5B). The threaded conductor 318 has a threaded section 320 with threads 322 extending radially outward from and helically around the threaded section 320. An outer ring 324 is a substantially cylindrical ring that defines the radially outer extent of the threaded conductor 318. A shoulder 326 is positioned axially between the outer ring 324 and the threaded section 320. The shoulder 326 is substantially cylindrical, with a diameter less than that of the outer ring 324 but greater than that of the threaded section 320. The threaded conductor 318 has an inner surface 328 defining a lumen extending through the threaded conductor 318.

A ridged section 330 is positioned adjacent the threaded section 320, axially between the threaded section 320 and the shoulder 326. The ridged section 330 includes a plurality of ridges 332 extending radially outward from an outer surface of the ridged section 330. The ridges 332 extend from the shoulder 326 to the threads 322.

FIG. 6B is a side view of the threaded conductor 318, showing the ridges 322 extending substantially axially from the shoulder 326 to the threads 322. A coil conductor (such as the outer coil conductor 76) can be attached to the threaded conductor 318 by threading the outer coil conductor 76 between the threads 322 such that one or more coils of the outer coil conductor 76 extends distally past the threads 322 and lies on one or more of the ridges 332. Thus, when a sleeve (such as the sleeve 124) is pressed on the outer coil conductor 76, the sleeve 124 can press one or more coils of the outer coil conductor 76 between the threads 322 and also press one or more coils of the outer coil conductor 76 against the ridges 332. The ridges 332 can resist circumferential movement by the outer coil conductor 76, helping to retain the outer coil conductor 76 in place, as well as encourage electrical contact between the outer coil conductor 76 and the threaded conductor 318. In one embodiment, the ridges 332 can be configured with a size, shape, and strength such that the ridges 332 deform when the sleeve 124 compresses the outer coil conductor 76 between the ridges 332 and the sleeve 124. In another embodiment, the outer coil conductor 76 can be covered by a layer of insulation and the ridges 332 can be relatively hard and sharp such that pressing the sleeve 124 axially over the coil conductor 76 causes the ridges 332 to cut through the layer of insulation to contact the coil conductor 76.

Figure 7B:
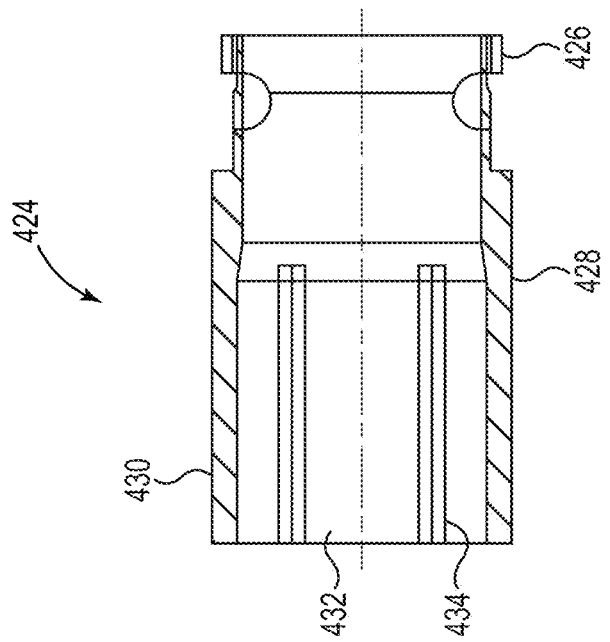
FIG. 7B is a side sectional view of the sleeve of FIG. 7A.
Figure 7A:
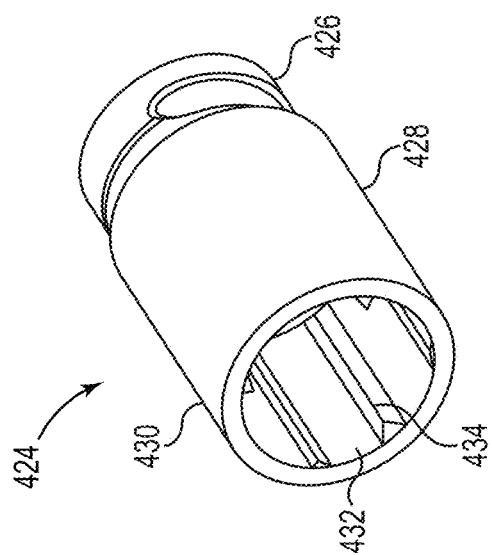
FIG. 7A is an isometric view of an alternative embodiment of a sleeve.

FIG. 7A is an isometric view of a sleeve 424, which is an alternative embodiment of the sleeve 124 (shown in FIGS. 3B and 4). The sleeve 424 has a proximal section 426 and a distal section 428. The sleeve 424 is substantially annular, with an outer surface 430 and an inner surface 432. The outer surface 430 is shaped and configured at the proximal section 426 for extending inside and connecting to the flexible body 44 (shown in FIGS. 2A, 2B, 3A, and 3B). The outer surface 430 is substantially cylindrical and smooth at the distal section 428 for use as a contact surface of the ring electrode assembly 78 (shown in FIGS. 3A and 3B). The inner surface 432 of the sleeve 424 has a plurality of ridges 434 that extend radially inward along the inner surface 432.

FIG. 7B is a side sectional view of the sleeve 424, showing the ridges 434 extending axially along the inner surface 432 of the sleeve 424. In the illustrated embodiment, the ridges 434 extend along the distal section 428 but terminate prior to the proximal section 426. In other embodiments, the ridges 434 can extend along an entire length of the inner surface 432 of the sleeve 424.

When the sleeve 424 is pressed on a coil conductor (such as the outer coil conductor 76) and a threaded conductor (such as threaded conductor 118), the ridges 434 of the inner surface 432 press the coil conductor 76 against the threaded section 120 of the threaded conductor 118. The ridges 434 can resist circumferential movement by the outer coil conductor 76, helping to retain the outer coil conductor 76 in place. In one embodiment, the ridges 434 can be configured with a size, shape, and strength such that the ridges 434 deform when the sleeve 124 compresses the outer coil conductor 76 between the ridges 434 and the sleeve 124.

Figure 8B:
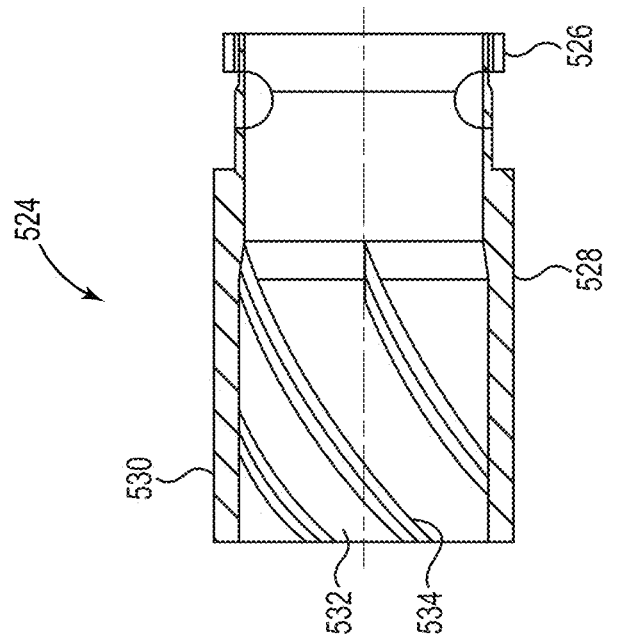
FIG. 8B is a side sectional view of the sleeve of FIG. 8A.
Figure 8A:
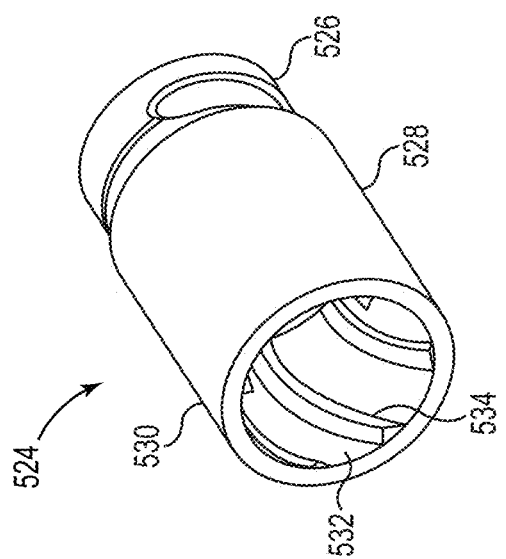
FIG. 8A is an isometric view of another alternative embodiment of a sleeve.

FIG. 8A is an isometric view of a sleeve 524, which is an alternative embodiment of the sleeves 124 (shown in FIGS. 3B and 4) and 424 (shown in FIGS. 7A and 7B). The sleeve 524 has a proximal section 526 and a distal section 528. The sleeve 524 is substantially annular, with an outer surface 530 and an inner surface 532. The sleeve 524 is substantially similar to the sleeve 424, except that the sleeve 524 has a plurality of ridges 534 that extend along the inner surface 532 in both axial and circumferential directions so as to be substantially helical.

FIG. 8B is a side sectional view of the sleeve 524. As shown in FIG. 8B, the ridges have a pitch of about 45 degrees with respect to axial in the illustrated embodiment. In other embodiments, the pitch of the ridges 534 can be varied.

When the sleeve 524 is pressed on a coil conductor (such as the outer coil conductor 76) and a threaded conductor (such as threaded conductor 118), the ridges 534 of the inner surface 532 press the coil conductor 76 against the threaded section 120 of the threaded conductor 118. The ridges 534 can be angled so as to cross the coils of the outer coil conductor 76, pressing the outer coil conductor 76 against the threaded conductor 118.

Figure 9:
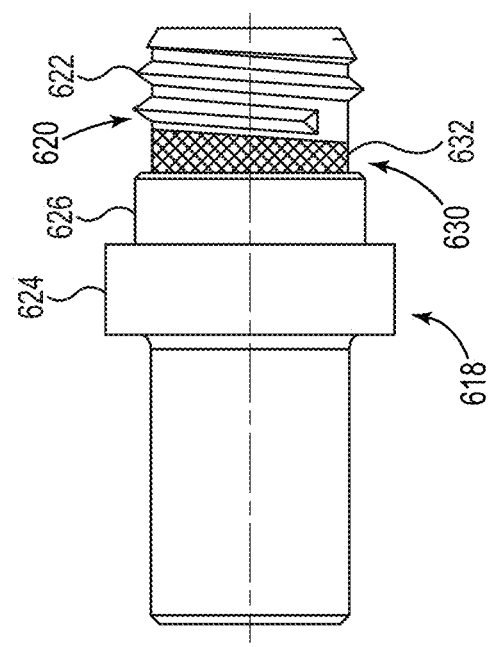
FIG. 9 is a side view of another alternative embodiment of a threaded conductor.

FIG. 9 is a side view of a threaded conductor 618, which is an alternative embodiment of the threaded conductors 118 (shown in FIGS. 3A, 3B, and 4), 218 (shown in FIGS. 5A and 5B), and 318 (shown in FIGS. 6A and 6B). The threaded conductor 618 has a threaded section 620 with threads 622 extending radially outward from and helically around the threaded section 620. An outer ring 624 is a substantially cylindrical ring that defines the radially outer extent of the threaded conductor 618. A shoulder 626 is positioned axially between the outer ring 624 and the threaded section 620. The shoulder 626 is substantially cylindrical, with a diameter less than that of the outer ring 624 but greater than that of the threaded section 620.

A knurled section 630 is positioned adjacent the threaded section 620, axially between the threaded section 620 and the shoulder 626. The knurled section 630 has a positive knurl that includes a plurality of knurls 632 extending radially outward from an outer surface of the knurled section 630 in a knurled pattern. In the illustrated embodiment, the knurled section 630 has a diamond-pattern knurling. In an alternative embodiment, the knurled section 630 can have a pattern created by a plurality of staggered sinusoidal cuts crossing one-another so as to create the knurls 632. A coil conductor (such as the outer coil conductor 76) can be attached to the threaded conductor 618 by threading the outer coil conductor 76 between the threads 622 such that one or more coils of the outer coil conductor 76 extends distally past the threads 622 and lies on one or more of the knurls 632. Thus, when a sleeve (such as the sleeve 124) is forced axially over the outer coil conductor 76, the sleeve 124 can press one or more coils of the outer coil conductor 76 between the threads 622 and also press one or more coils of the outer coil conductor 76 against the knurls 632. The knurls 632 can resist circumferential movement by the outer coil conductor 76, helping to retain the outer coil conductor 76 in place, as well as encourage electrical contact between the outer coil conductor 76 and the threaded conductor 618.

Figure 10:
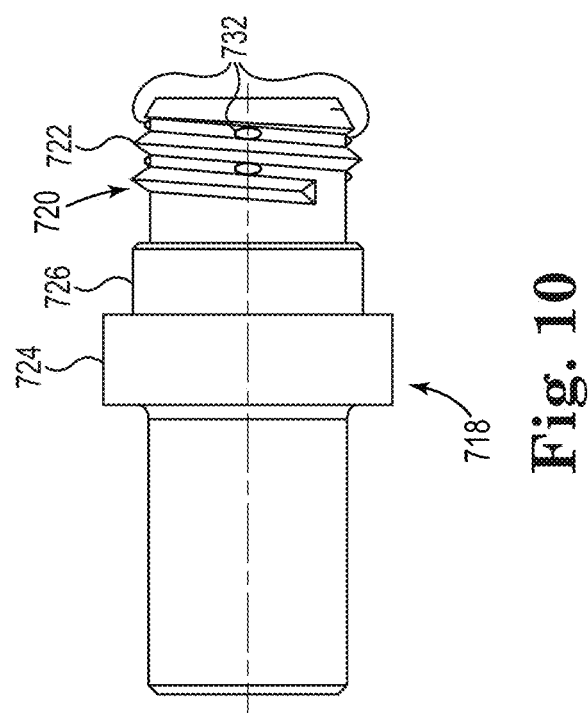
FIG. 10 is a side view of another alternative embodiment of a threaded conductor.

FIG. 10 is a side view of a threaded conductor 718, which is an alternative embodiment of the threaded conductors 118 (shown in FIGS. 3A, 3B, and 4), 218 (shown in FIGS. 5A and 5B), 318 (shown in FIGS. 6A and 6B), and 618 (shown in FIG. 9). The threaded conductor 718 has a threaded section 720 with threads 722 extending radially outward from and helically around the threaded section 720. An outer ring 724 is a substantially cylindrical ring that defines the radially outer extent of the threaded conductor 718. A shoulder 726 is positioned axially between the outer ring 724 and the threaded section 720. The shoulder 726 is substantially cylindrical, with a diameter less than that of the outer ring 724 but greater than that of the threaded section 720.

The threaded conductor 718 has a plurality of bumps 732 extending radially outward from the threaded conductor 718. The bumps 732 are positioned between adjacent threads 722 of the threaded section 720. In the illustrated embodiment, the bumps 732 are positioned periodically every 90 degrees around the threaded section 720 and are patterned helically between the helical threads 722. In an alternative embodiment, the bumps 732 can be positioned differently than as illustrated, such as being positioned on only one side of the threaded conductor 718. The threaded conductor 718 can be created using a screw cutting process, whereby the threaded conductor is rotated and translated axially while a cutter cuts the threads 722 into the threaded section 720. The bumps 732 can be formed by moving the cutter radially outward and then radially back inward at each location of the bumps 732. The shape, radial height, and circumferential length of the bumps 732 can be varied as suitable for the application.

A coil conductor (such as the outer coil conductor 76) can be attached to the threaded conductor 718 by threading the outer coil conductor 76 between the threads 722. The outer coil conductor 76 can contact and be pushed radially outward by one or more of the bumps 722 as the outer coil conductor 76 extends around the threaded conductor 718. Thus, when a sleeve (such as the sleeve 124) is forced axially over the outer coil conductor 76, the sleeve 124 can press one or more coils of the outer coil conductor 76 against the bumps 732. The bumps 732 can resist circumferential movement by the outer coil conductor 76, helping to retain the outer coil conductor 76 in place, as well as encourage electrical contact between the outer coil conductor 76 and the threaded conductor 718. In one embodiment, the outer coil conductor 76 can be covered by a layer of insulation and the bumps 732 can be relatively hard and sharp such that pressing the sleeve 124 axially over the coil conductor 76 causes the bumps 732 to cut through the layer of insulation to contact the coil conductor 76.

Figure 11:
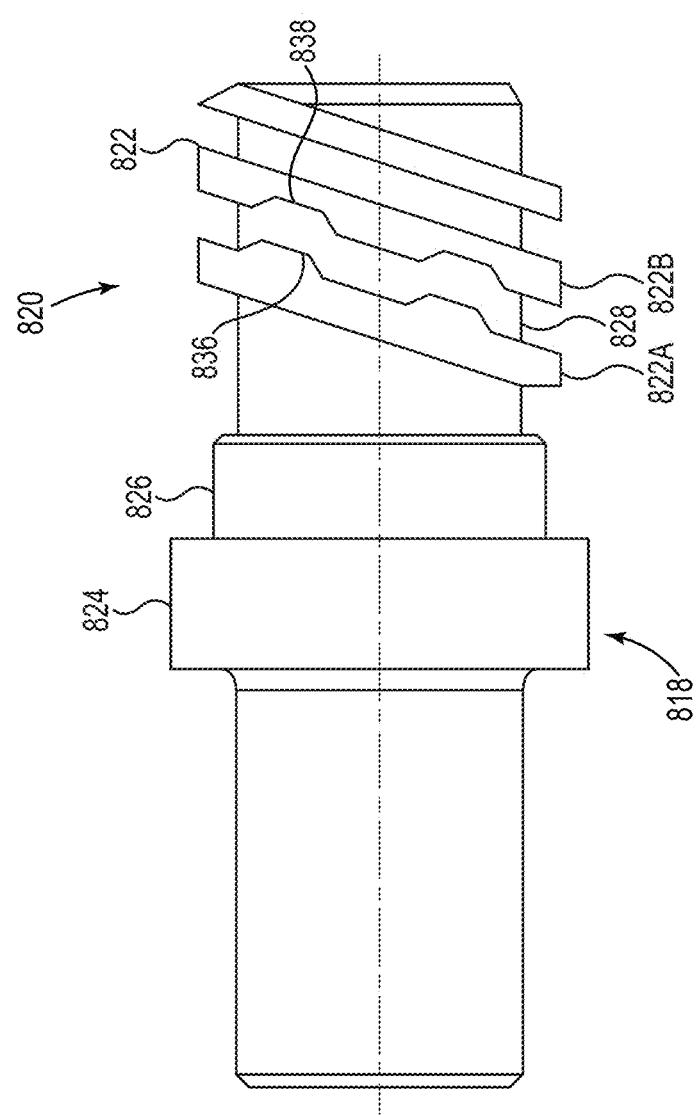
FIG. 11 is a side view of another alternative embodiment of a threaded conductor.

FIG. 11 is a side view of a threaded conductor 818, which is an alternative embodiment of the threaded conductors 118 (shown in FIGS. 3A, 3B, and 4), 218 (shown in FIGS. 5A and 5B), 318 (shown in FIGS. 6A and 6B), 618 (shown in FIG. 9), and 718 (shown in FIG. 10). The threaded conductor 818 has a threaded section 820 with threads 822 (including threads 822A and 822B) extending radially outward from and helically around the threaded section 820. An outer ring 824 is a substantially cylindrical ring that defines the radially outer extent of the threaded conductor 818. A shoulder 826 is positioned axially between the outer ring 824 and the threaded section 820. The shoulder 826 is substantially cylindrical, with a diameter less than that of the outer ring 824 but greater than that of the threaded section 820. The threads 822 define grooves 828 between the threads 822. In the illustrated embodiment, the threads 822 are square threads and the grooves 828 are square grooves.

The threaded conductor 818 has bumps 836 and recesses 838 extending from the threads 822. In the illustrated embodiment, the bumps 836 are on a proximal side (with respect to the longitudinal axis 54 of the lead 14, shown in FIG. 2A) of the thread 822A and the recesses are on a distal side of the thread 822B. The bumps 836 extend axially in a proximal direction from the thread 822A toward the thread 822B. The recesses 838 extend axially in a distal direction into the thread 822B, away from the thread 822A. The recesses 838 are each aligned opposite a corresponding one of the bumps 836. The bumps 836 and the recesses 838 distort the otherwise helical path of the groove 828.

A coil conductor (such as the outer coil conductor 76) can be attached to the threaded conductor 818 by threading the outer coil conductor 76 between the threads 822. The bumps 836 can push against and elastically bend one or more coils of the outer coil conductor 76. The recesses 838 can provide space opposite the bumps 836 for the outer coil conductor 76 to be displaced. In alternative embodiments, the recesses 838 can be omitted and the bumps 836 can compress the outer coil conductor 76 against a distal side of the thread 822B, which can compress and/or bend the outer coil conductor 76 elastically or plastically. In one embodiment, the bumps 836 and recesses 838 can retain the outer coil conductor 76 between the threads 822 without use of an outer sleeve. In an alternative embodiment, a sleeve (such as the sleeve 124) can be forced axially over the outer coil conductor 76 to press one or more coils of the outer coil conductor 76 against the threaded conductor 818.

Figure 12:
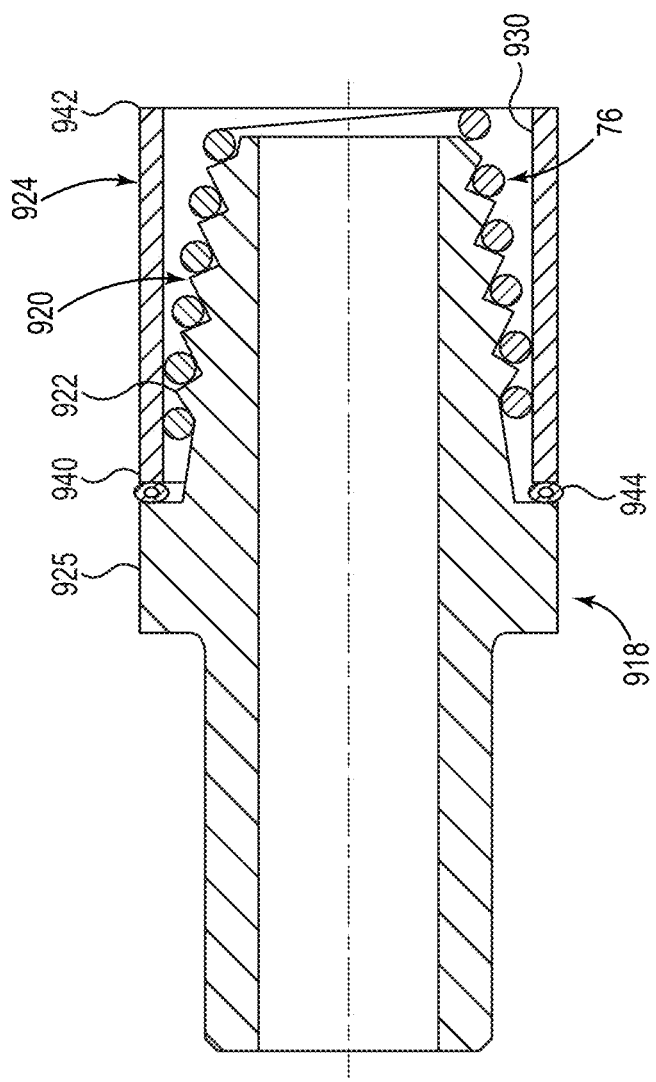
FIG. 12 is a schematic cross-sectional view of another alternative embodiment of a threaded conductor and a corresponding sleeve.

FIG. 12 is a schematic cross-sectional view of a threaded conductor 918 and a corresponding sleeve 924, which are alternative embodiments of threaded conductors and sleeves described above. The threaded section 920 of the threaded conductor 918 tapers in the proximal direction and the radially inner surface 930 of the sleeve 924 is substantially cylindrical. Thus, the outer coil conductor 76 is compressed between the threaded section 920 and a distal end 940 of the sleeve 924, but is not compressed between the threaded section 920 and a proximal end 942 of the sleeve 924.

A seal ring 944 can be positioned axially between the distal end 940 of the sleeve 924 and an outer ring 925 of the threaded conductor 918. The seal ring 944 can be used to seal a gap formed between the sleeve 924 and the outer ring 925 due to the taper of the threaded section 920. The seal ring 944 can be welded between the sleeve 924 and the outer ring 925 to hermetically seal the interface between the sleeve 924 and the outer ring 925. A force can be exerted on the sleeve 924 in an axially direction toward the outer ring 925 during welding of the seal ring 944. In one embodiment, the seal ring 944 can be made from relatively soft platinum. In alternative embodiments, the seal ring 944 can be made from another metal that is relatively soft and compressible and that is suitable for welding to both the threaded conductor 918 and the sleeve 924. In the illustrated embodiment, the seal ring 944 has a circular cross section. In alternative embodiments, the seal ring 944 can have a different shape, such as an arc-shaped, diamond-shaped, or cross-shaped cross section.

Figure 13:
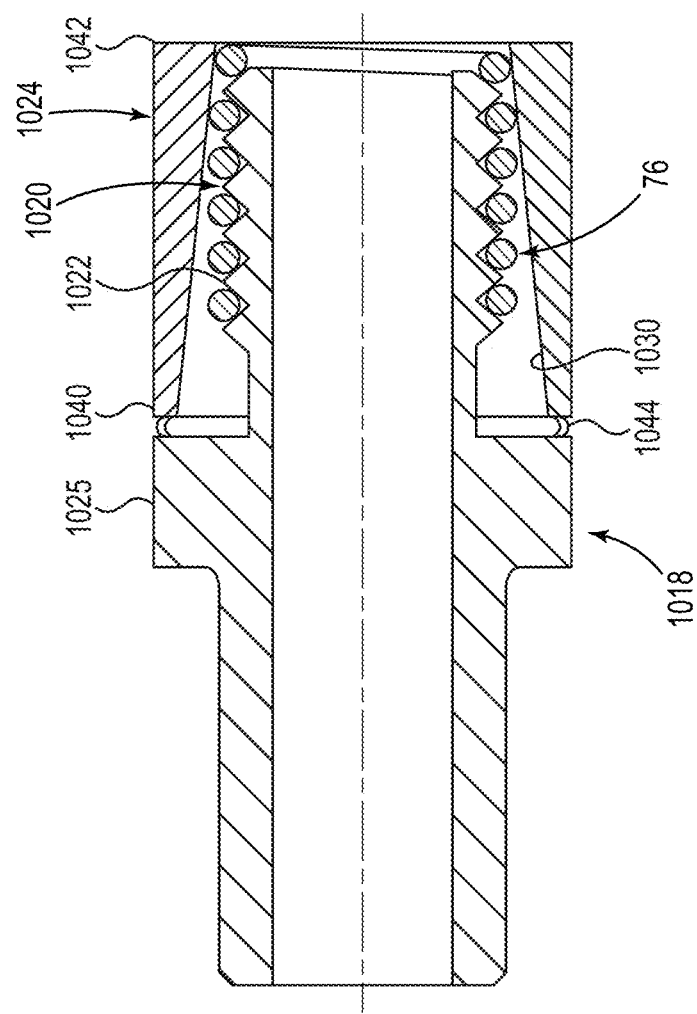
FIG. 13 is a schematic cross-sectional view of another alternative embodiment of a threaded conductor and a corresponding sleeve.

FIG. 13 is a schematic cross-sectional view of a threaded conductor 1018 and a corresponding sleeve 1024, which are alternative embodiments of threaded conductors and sleeves described above. The radially inner surface 1030 of the sleeve 1024 tapers in the proximal direction and the threaded section 1020 of the threaded conductor 1018 is substantially cylindrical (excepting the helical shape of threads 1022). Thus, the outer coil conductor 76 is compressed between the threaded section 1020 and a proximal end 1042 of the sleeve 1024, but is not compressed between the threaded section 1020 and a distal end 1040 of the sleeve 1024.

A seal ring 1044 can be positioned axially between the distal end 1040 of the sleeve 1024 and an outer ring 1025 of the threaded conductor 1018. The seal ring 1044 can be used to seal a gap formed between the sleeve 1024 and the outer ring 1025 due to the taper of the radially inner surface 1030 of the sleeve 1024. The seal ring 1044 can be welded between the sleeve 1024 and the outer ring 1025 to hermetically seal the interface between the sleeve 1024 and the outer ring 1025. In the illustrated embodiment, the seal ring 1044 has an arc-shaped cross section. In alternative embodiments, the seal ring 1044 can have a different shape, such as a circular, diamond-shaped, or cross-shaped cross section.

FIG. 14 is a schematic cross-sectional view of a threaded conductor 1118 and a corresponding sleeve 1124, which are alternative embodiments of threaded conductors and sleeves described above. The threaded conductor 1118 has an outer ring 1125, a threaded section 1120, and a shoulder 1126 between the outer ring 1125 and the threaded section 1120. The radially inner surface 1130 of the sleeve 1124 is stepped so as to have a first inner surface section 1130A and a second inner surface section 1130B. The first inner surface section 1130A is positioned at a distal end 1140 of the sleeve 1124 and has a diameter substantially the same as a diameter of the shoulder 1126. The second inner surface section 1130B is positioned at the proximal end 1142 of the sleeve 1124 and has a diameter smaller than the diameter of the first inner surface section 1130A.

When the sleeve 1124 is pushed axially over the threaded conductor 1118 and the coil conductor 76, the first inner surface section 1130A is in contact with the shoulder 1126 and the second inner surface section 1130B pushes the coil conductor 76 radially inward against the threaded section 1120. The sleeve 1124 can be pushed axially far enough that the distal end 1140 of the sleeve 1124 is in contact with the outer ring 1125, or can be pushed near but spaced from the outer ring 1125 as illustrated. The distal end 1140 can be welded to the outer ring 1125 and/or the shoulder 1126 to form a hermetic seal. Alternatively, a seal ring (such as seal rings 944 and 1044 shown in FIGS. 12 and 13) can be utilized.

Thus, a coil conductor for a medical electrical lead can be connected between first and second conductors in an interference fit as described above in various embodiments. The interference fit can help provide a relatively reliable mechanical and electrical connection between the coil conductor and the first and second conductors. Either the first or the second conductor (whether radially inward or outward of the coil conductor) can have threads that can help hold the coil conductor in place during assembly, and also can retain the coil conductor after assembly. In some embodiments, the coil conductor can also be welded to the first and/or the second conductor to further improve the mechanical and electrical connection therebetween. Either or both of the first and second conductors can include one or more ridges or bumps that press against the coil conductor. While the above description focuses on connections in cardiac electrical leads, in some embodiments such connections can be used in other medical electrical leads using a coil conductor, such as in neurostimulation devices.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. One or more features from one of the embodiments can be combined with one or more features described and illustrated with respect to one or more of the other embodiments. Accordingly, the scope of the present invention is intended to embrace all such alternatives, modifications, and variations as fall within the scope of the claims, together with all equivalents thereof.

We claim:

1. A medical electrical lead comprising:
a threaded conductor having an outer surface with a threaded section that includes threads that are helical and that define grooves between the threads;
a coil conductor having coils seated in the grooves of the threaded conductor, wherein the coil conductor has a coil major diameter greater than a thread major diameter; and
a sleeve positioned radially outward of the coil conductor and having an outer surface that is an outermost surface of the medical electrical lead and an inner surface in direct contact with the coil conductor so as to produce a radially inward force compressing the coil conductor against the threaded section of the threaded conductor.

2. The medical electrical lead of claim 1, wherein the coil conductor is welded to the threaded section.

3. The medical electrical lead of claim 1, wherein the inner surface of the sleeve comprises a plurality of ridges extending longitudinally from one end of the sleeve toward another end of the sleeve and radially inward to directly contact the coil conductor.

4. The medical electrical lead of claim 1, wherein the threaded conductor has a ridged section adjacent the threaded section.

5. The medical electrical lead of claim 4, wherein the ridged section has a plurality of ridges extending radially outward from the outer surface in an axial direction with respect to a centerline axis of the threaded conductor, and wherein the coil conductor is compressed between the ridges and the sleeve.

6. The medical electrical lead of claim 4, wherein the ridged section has a knurled pattern.

7. The medical electrical lead of claim 1, wherein at least one of the threaded section and the inner surface is substantially conical.

8. The medical electrical lead of claim 1, wherein both the threaded section and the inner surface are substantially conical.

9. The medical electrical lead of claim 1, wherein the inner surface of the sleeve is spaced from the threads.

10. The medical electrical lead of claim 1, wherein at least one of the threaded conductor and the sleeve comprises an electrode for delivering an electrical stimulation to or for sensing an electrical signal from body tissue.

11. The medical electrical lead of claim 1, wherein the threaded conductor and the sleeve combine to form a ring electrode assembly.

12. The medical electrical lead of claim 1, wherein the threaded conductor comprises at least one bump extending radially outward from the outer surface between threads in contact with the coil conductor.

13. The medical electrical lead of claim 1, and further comprising:

a seal ring positioned axially between the sleeve and an outer ring of the threaded conductor, wherein the seal ring is hermetically welded between the sleeve and the threaded conductor.

14. A medical electrical lead comprising:

a first conductor having a threaded section that includes threads that are helical and that define grooves between the threads, wherein at least one of the threads comprises a bump that distorts a helical path between the threads to provide a distorted helical path between the threads;

a coil conductor having coils seated in the grooves between the threads of the first conductor, wherein one of the coils of the coil conductor has a bend in an axial direction and a shape of the distorted helical path between the threads; and a second conductor axially aligned with the threaded section of the first conductor, with the coils of the coil conductor positioned between the first conductor and the second conductor.

15. The medical electrical lead of claim 14, wherein the bump is one of a plurality of bumps extending axially from the threads, and wherein the threads further comprise a plurality of recesses each aligned opposite of one of the plurality of bumps.

16. The medical electrical lead of claim 14, wherein an interference fit compresses the coil conductor between the second conductor and the threaded section.

17. The medical electrical lead of claim 14, wherein the threads extend from an outer surface of the first conductor and wherein the second conductor is a sleeve positioned radially outward of the first conductor.

18. The medical electrical lead of claim 14, wherein the one of the coils is compressed between the bump and an opposing un-recessed side of the at least one of the threads.

* * * * *